United States Patent

Kaali et al.

[11] Patent Number: 4,770,167
[45] Date of Patent: Sep. 13, 1988

[54] ELECTRICAL, GENERALLY ROUNDED RESILIENT, CANOPY-LIKE CONTRACEPTIVE DEVICES

[76] Inventors: Steven Kaali, Penthouse E, 225 E. 23rd. St., New York, N.Y. 10021; Peter M. Schwolsky, 4101 Cathedral Ave., NW., Washington, D.C. 20016

[21] Appl. No.: 68,417

[22] Filed: Jul. 1, 1987

Related U.S. Application Data

[63] Continuation-in-part of Ser. No. 059,943, Jun. 9, 1987, abandoned.

[51] Int. Cl.⁴ .................................................. A61F 5/46
[52] U.S. Cl. .................................. 128/788; 128/783; 128/833
[58] Field of Search ............... 128/130, 127, 131, 788, 128/783, 784, 775, 778; 604/891; 429/16 C

[56] References Cited

U.S. PATENT DOCUMENTS

| | | | |
|---|---|---|---|
| 353,346 | 11/1886 | Baldwin | 128/788 |
| 520,206 | 5/1894 | Hinkley | 128/788 |
| 520,895 | 6/1894 | Petit | 128/788 |
| 662,716 | 11/1900 | Gaedeke | 128/788 |
| 3,411,507 | 11/1968 | Wingrove | 128/784 |
| 3,749,089 | 7/1973 | Derr | 128/738 |
| 3,901,224 | 8/1975 | Bucalo | 128/130 |
| 3,973,571 | 8/1976 | Suhel | 128/788 |
| 4,031,365 | 6/1977 | Raggiotti et al. | 128/738 |
| 4,577,640 | 3/1986 | Hofmeister | 128/738 |
| 4,616,640 | 10/1986 | Kaali et al. | 128/788 |

Primary Examiner—Robert A. Hafer
Assistant Examiner—Charles H. Sam
Attorney, Agent, or Firm—Charles W. Helzer

[57] ABSTRACT

An electrical having electric field producing electrodes either on the exterior or the interior surfaces, or both, of either an electrical cervical cap or an electrical diaphragm and supplying the electrodes with electric potential from miniaturized electrical cells embedded within an enlarged circular rim portion that surrounds the open mouth end of the device. Electrical is provided by the electrically excited electrodes and acts in conjunction with the cervical cap or diaphragm to prevent the migration of male sperm into the open end of the cervical canal of a female human being or other mammal. The electrical cervical cap or diaphragm device can be designed such that it is open at the apex and does not impede the free flow of menstrual and other fluid discharges through the cervical canal. It is fabricated with or covered by biologically inert material so that it can be retained in place in the cervical canal for indefinite periods as long as desired by the user for birth control purposes. The electrical cervical cap or electrical diaphragm thus designed acts not only as an effective birth control measure to prevent the migration of male sperm through the cervical canal into the uterus, but also appears to function as an anti-bacterial and/or anti-viral device.

36 Claims, 4 Drawing Sheets

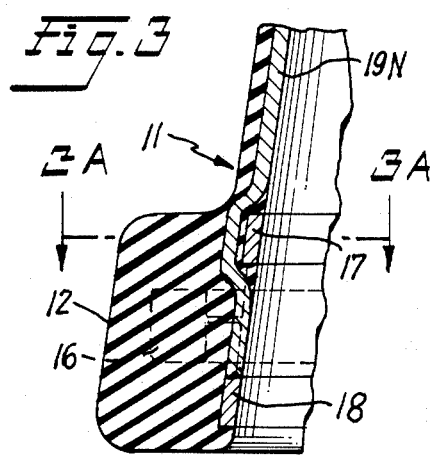
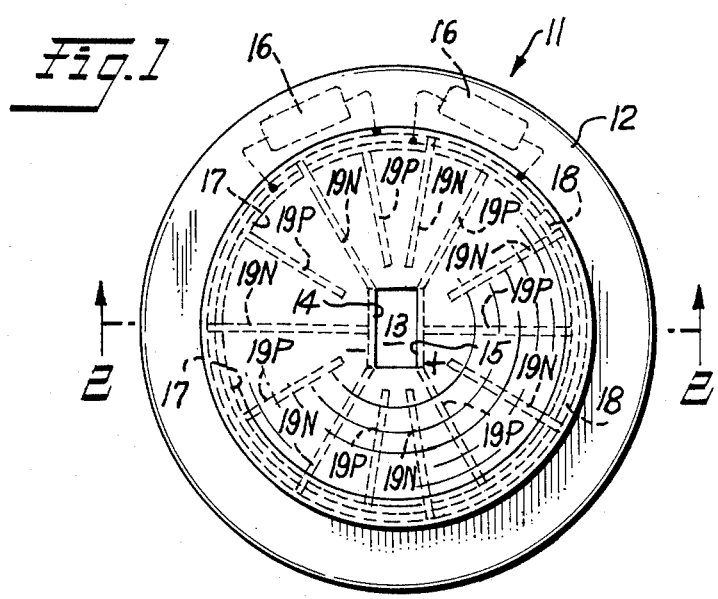
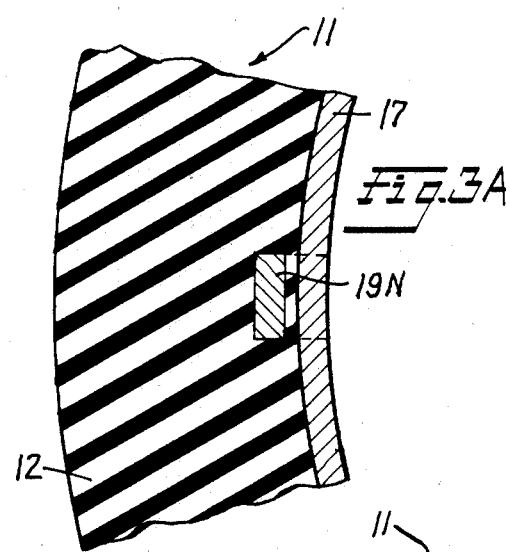
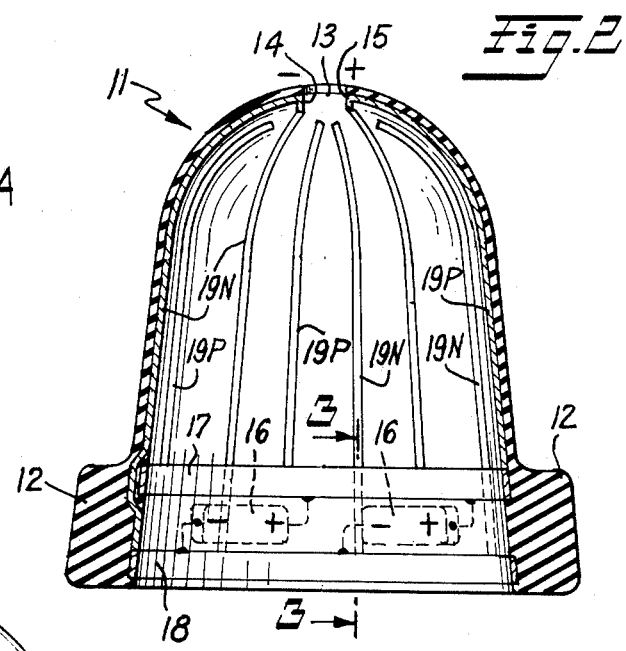
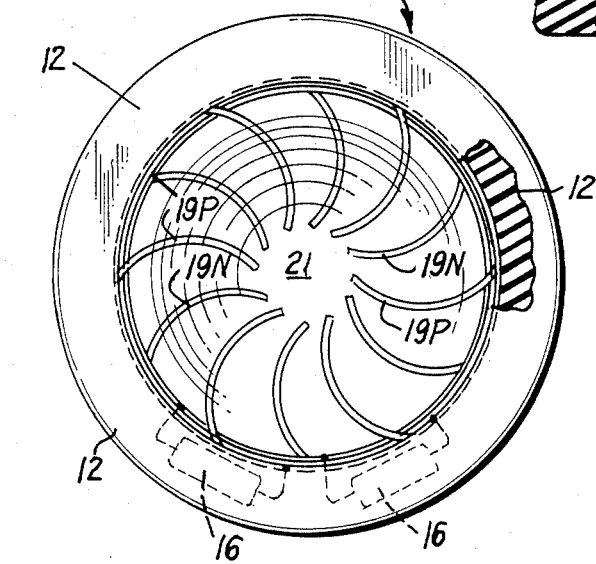

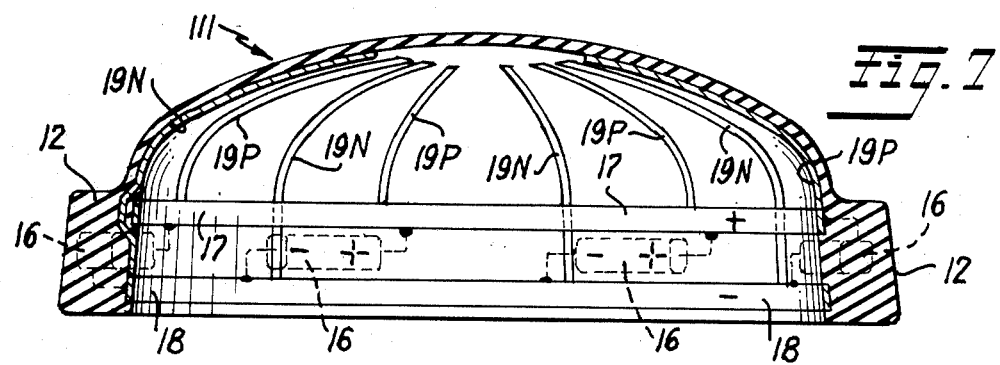
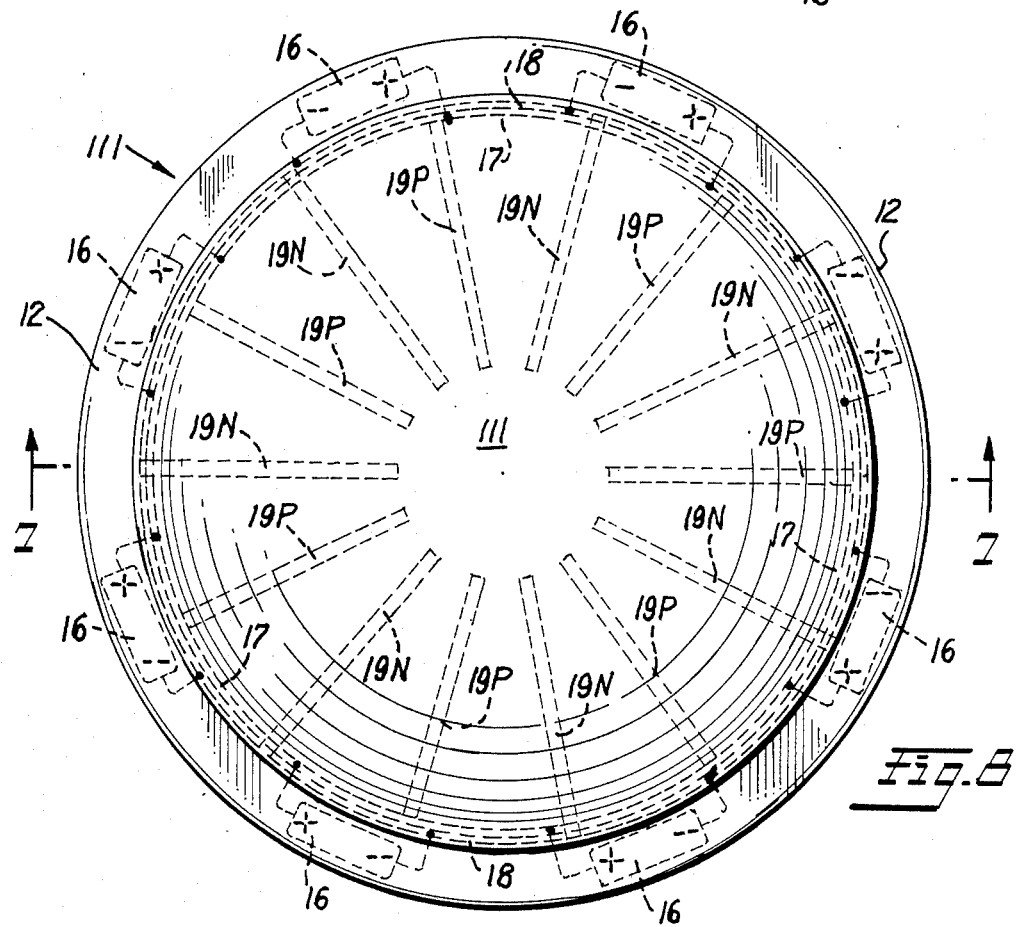
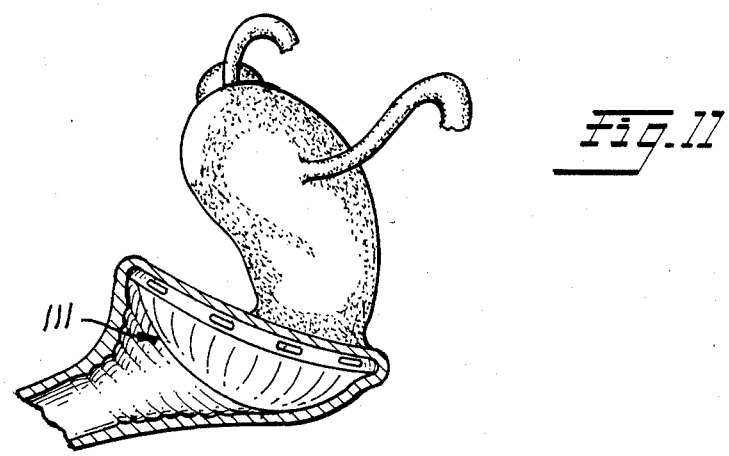

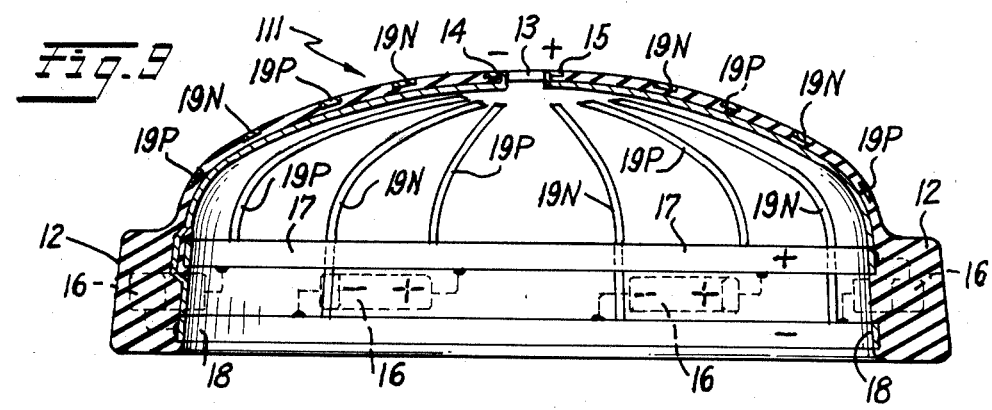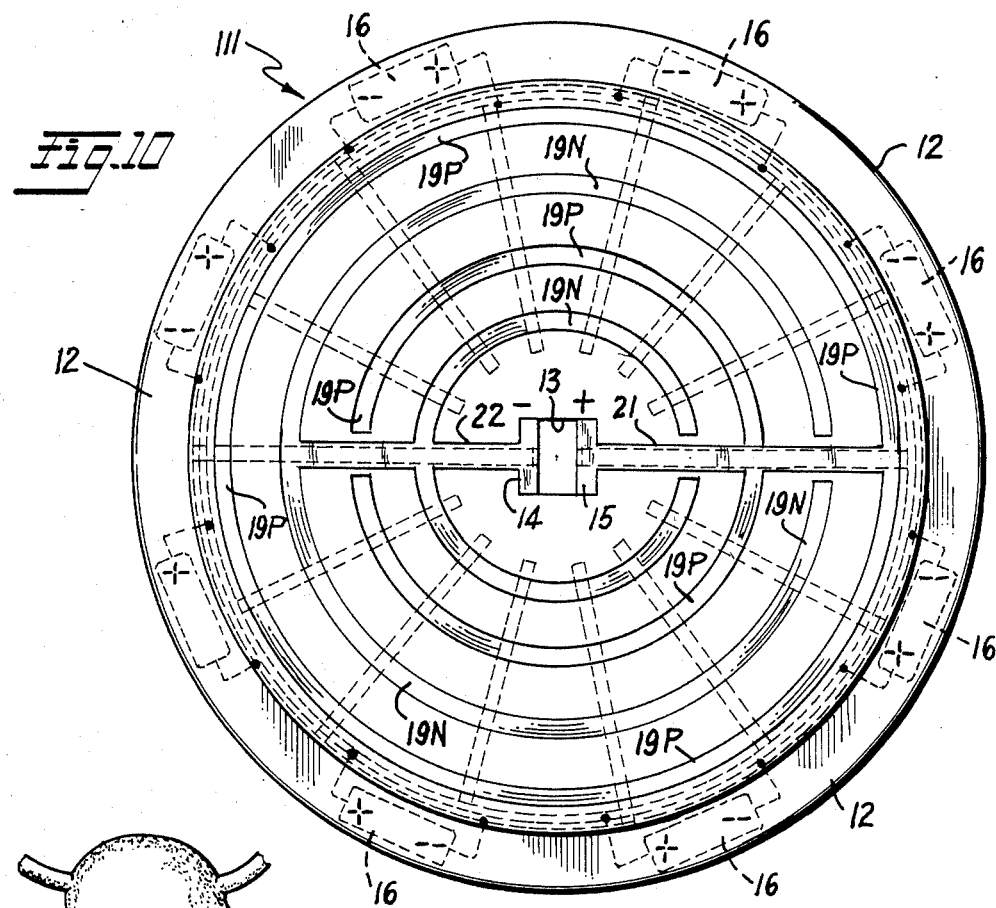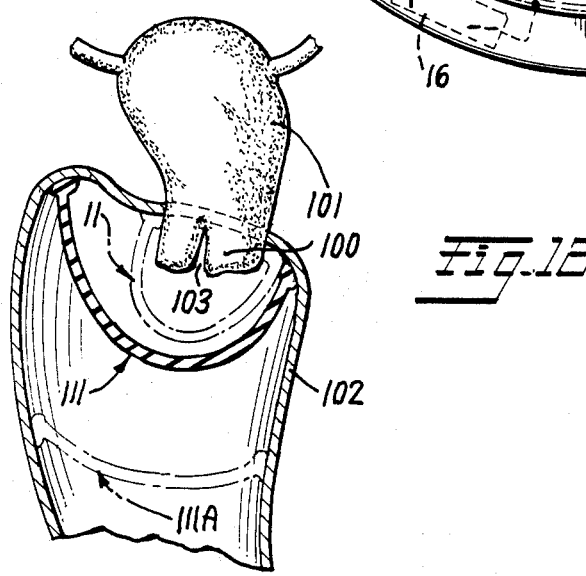

ELECTRICAL, GENERALLY ROUNDED RESILIENT, CANOPY-LIKE CONTRACEPTIVE DEVICES

The present invention is an improvement in the electrical method and device for contraception described in U.S. Pat. No. 4,616,640; and is a continuation-in-part of U.S. application Ser. No. 059,943 filed June 9, 1987 now abandoned.

FIELD OF INVENTION

This invention relates to the field of birth control methods and contraceptive devices for use by human females as well as females of most quadrupeds and other mammals.

BACKGROUND OF INVENTION

U. S. Pat. No. 4,616,640 for a "Birth Control Method and Device Employing Electric Forces"—issued Oct. 14, 1986—by Steven Kaali, Peter M. Schwolsky and Joseph W. Porter, inventors, discloses a novel method and device using electric forces within and about the cervical canal of a female for acting on male sperm and preventing migration of the male sperm through the cervical canal and into the uterine cavity where it might fertilize an egg.

SUMMARY OF INVENTION

A principle object of the invention is to provide an improved electrical force birth control method and contraceptive device employing an electrical generally rounded, resilient canopy-like protective enclosure of the cervical cap or the diaphragm-type of construction.

In practicing the invention, a birth control method and contraceptive device is provided which utilizes generally rounded, resilient a canopy-like protective enclosure comprising either an electrical cervical cap or electrical diaphragm to be fitted within the vagina of a human or other female animal. The electrical cervical cap and electrical diaphragm devices have formed thereon a set of spaced-apart electrically conductive electrodes of biologically inert, conductive material compatible with human and other animal tissue. The devices further include means for supplying an electromotive force of known voltage and current rating across the set of electrodes from an independent source of electric potential for producing an electrical force within and about the cervical canal of the female human or other animal. In preferred embodiments of the invention either an electrical cervical cap or an electrical diaphragm is provided, either of which is inserted in the vagina to provide a generally rounded, resilient canopy-like protective enclosure over the opening in the cervix to the cervical canal of a female human being or other mammal. The electrical cervical cap has a thimble-like configuration and is designed to closely fit over the cervix within the vagina. The electrical diaphragm is essentially disc-shaped and is designed to fit within the vagina but not so closely over the cervix. Both devices are made from latex or other medical grade elastomer or similar material which is compatible with human and animal tissue. Both devices are provided with spaced-apart electrode members either on the exterior surface (away from the cervix) or the interior surface (facing the cervix) or on both sides and are provided with different polarity electric excitation potentials for producing an electric field gradient between the electrode members. In one particular embodiment of the invention a central opening is provided in the apex of either the electrical cervical cap or the electrical diaphragm so that the device can be worn over prolonged periods of time since it will allow body fluids to drain through the opening.

In other specific embodiments of the invention, no central opening is provided in the apex of either the electrical cervical cap or the electrical diaphragm so that either device can be worn only over short periods of time during the mid-cycle period.

BRIEF DESCRIPTION OF DRAWINGS

These and other objects, features and many of the attendant advantages of this invention will be appreciated more readily as the same becomes better understood from a reading of the following detailed description considered in connection with the accompanying drawings, wherein like parts in each of the several figures are identified by the same reference characters and wherein:

FIG. 1 is an enlarged top plan view of an electrical cervical cap-type contraceptive device according to the present invention;

FIG. 2, is a vertical sectional view taken on the line 2—2 of FIG. 1;

FIG. 3 is an enlarged fragmentary vertical sectional view taken on the line 3—3 of FIG. 2;

FIG. 3A is a further enlarged fragmentary horizontal sectional view taken on the line 3A—3A of FIG. 3;

FIG. 4 is an enlarged top plan view, partly in section, of a second and preferred form of electrical cervical cap-type contraceptive device according to the invention;

FIG. 7 is an enlarged cross-sectional view taken substantially through plane 7—7 of FIG. 8 illustrating the details of construction of an electrical diaphragm-type of contraceptive device according to the invention;

FIG. 8 is a top plan view of the electrical diaphragm shown in cross-section in FIG. 7;

FIG. 9 is a cross-sectional view taken through plane 9—9 of FIG. 10 of a modified form of electrical diaphragm according to the invention wherein a central opening is provided in the apex of the electrical diaphragm;

FIG. 10 is a top plan view of the electrical diaphragm shown in cross-section in FIG. 9;

FIG. 11 is a side sectional view of an electrical diaphragm such as shown in FIG. 7 inserted in the vagina of a female human being and illustrates how the electrical diaphragm forms a canopy-like protective enclosure over the cervix; and FIG. 12 is an outline view of the vagina and uterus of a female human being illustrating the difference in construction and manner of support between the electrical cervical cap and the electrical diaphragm, and further illustrates two different types of electrical diaphragms one of which is inserted in close proximity to the cervix and the other of which is inserted further down in the vagina and spaced from the cervix.

BEST MODE OF PRACTICING THE INVENTION

Figure 4A:
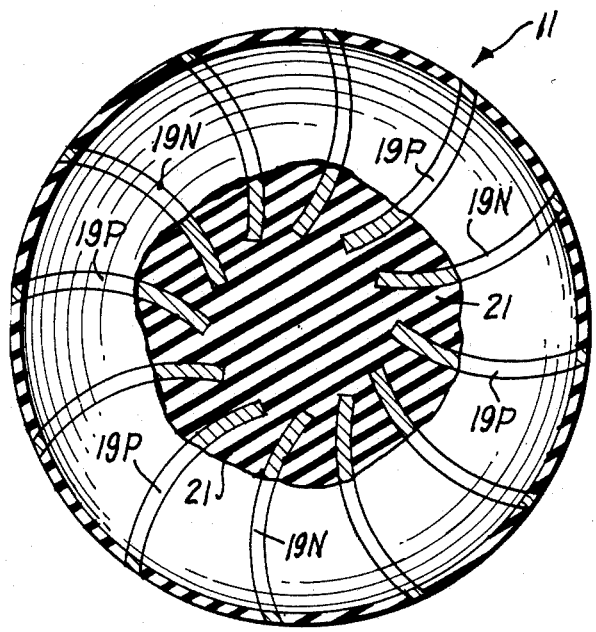
FIG. 4A is an enlarged fragmentary crosssectional view of the closed apex area of the device of FIG. 4 showing the integral insulating closure at the peak of the cap and the spaced-apart electrical conductors embedded therein.

The birth control method and contraceptive device made possible by this invention, similar to the invention described in U.S. Pat. No. 4,616,640, in operation provides an electric force which is operative within and about the cervical canal of a female so that the electrical force acts on and prevents active male sperm from passing through the cervical canal and fertilizing a female egg thereby providing a reliable and safe form of birth control. Accordingly, the disclosure of U.S. Pat. No 4,616,640 hereby is incorporated into the disclosure of this application in its entirety.

It still is not entirely clear in what manner the electrical force prevents male sperm from migrating up the cervical canal while employing an electrical contraceptive device. One theory is that an induced electric current is caused to flow through the mucous fluid normally discharged during mid-cycle by the female. The electric current flow through this mucous fluid in effect alters the nature of the mid-cycle mucous fluid so that it becomes an effective barrier to the transport of male sperm. A second theory is that an electrical force in the form of an electrostatic field acts on the active male sperm (known to possess an electrical charge) so as to cause electro-deposition of the sperm onto the electrically conductive electrodes thereby preventing further passage of the sperm through the cervical canal. A further theory which recently has been developed is that the electric field within the cervical mucous fluid or semen electrolyte causes ionization which in turn results in an ion current flow and bombardment of the sperm with ions thereby preventing their further passage up the cervical canal. It is altogether possible that some combination of two or all three of these theories is involved in the effective impediment and prevention of further migration of the male sperm up the cervical canal so that the method and device provides an effective birth control measure.

A still further and interesting feature is that the electrical contraceptive device, either in the form disclosed in U.S. Pat. 4,616,640 or as disclosed in this application, also performs an anti-bacterial and/or an anti-viral function to reduce possibility of infection in the uterus, the cervix and/or the vagina by either bacteria or virus. It is known that male sperm can carry with them bacteria and virus of certain types. The electric field forces and induced current produced by the electrical contraceptive device scours the bacteria both directly and by eliminating the male sperm carrier altogether thus preventing it together with entrained bacteria and/or virus from travelling up the vagina and cervical canal and into the uterine cavity. Similar killing of bacteria or virus either being introduced or already present in the vagina, cervix or cervical canal or uterus and fallopian tubes is achieved with the electrical contraceptive device.

Lastly, and equally important, is the realization that the semen of a male human or animal can and does function as an electrolyte both during operation and to initiate operation of the device. Thus in those embodiments where the presence of fluids is used to initiate activation of the electrical contraceptive device, the occurrence of semen in the vagina or around the opening to the cervical canal with the electrical conceptive device in place, would serve to activate the device and prevent sperm from progressing through the cervical canal to the uterine cavity.

FIG. 1 is a top plan view of one embodiment of an electrical generally rounded, resilient canopy-like protective enclosure for the cervix that comprises a novel electrical cervical cap constructed in accordance with the invention and FIG. 2 is a longitudinal sectional view of the electrical cervical cap shown in FIG. 1 taken through plane II—II of FIG. 1. The cervical cap is shown generally at 11 in FIGS. 1 and 2 and is thimble-shaped with an enlarged rim portion 12 that circumferentially surrounds the open mouth end of the thimble-shaped cap. In this embodiment of the invention, intended for long term use by a wearer of the device, a small, central opening shown at 13 is formed in the apex of the thimble-shaped cervical cap. The central opening 13 is bracketed by a pair of spaced-apart, electrically conductive, plate or wire members 14 and 15 which are electrically isolated one from the other and are fabricated from materials such as platinum, platinum alloys or platinum coated polymers or other similar conductive material which is relatively inert and compatible with human fluids and tissue. The opening 13 is designed to be large enough to permit discharge of fluids from the cervical canal to flow out. Consequently, this embodiment of the invention can be left in place for longer periods of time thereby assuring its use during the critical mid-cycle ovulation period when cervical mucous fluid is present in the cervical canal.

Figure 6:
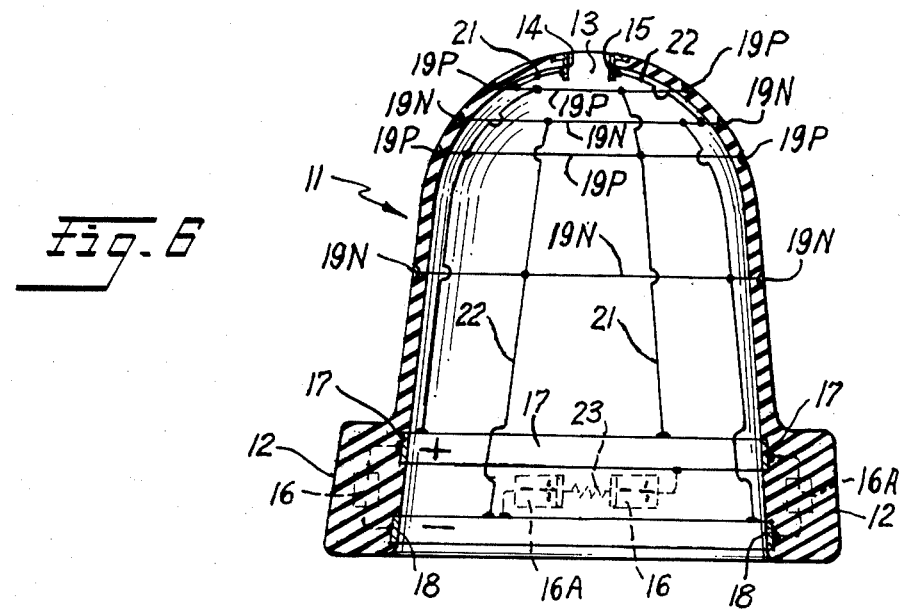
FIG. 6 is a longitudinal sectional view taken substantially along line 6—6 of FIG. 5.

As best seen in the fragmentary sectional view shown in FIGS. 3 and 3A, one or more miniaturized electrical cells 16 is embedded in the enlarged rim portion 12 of the cervical cap. The electrical cells 16 may be comprised by the Micro Power Cells TM series of lithium-iodine 2.8 volt solid CMOS cells manufactured and sold by Catalyst Research—a division of Mine Safety Appliances Company which is located in Baltimore, Md., or a similar cell. The number of such cells and their manner of interconnection, as best shown in FIGS. 2 and 6, is determined essentially by the design voltage and current rating desired for the contraceptive device. In this embodiment, as shown in FIGS. 1–3, the cells 16 are interconnected in parallel circuit relationship across a pair of circularly, electrically conductive bus bar terminal conductors 17 and 18 which are circumferentially formed around the inside surface of the enlarged rim portion 12 of the cervical cap and completely surround the open mouth end of the cap. The circular bus bar conductors 17 and 18 likewise preferably are formed from platinum or a platinum alloy or platinum coated polymers, but of course could be comprised of any suitable conductive material which is biologically compatible with human tissue and fluids and are exposed to fluids in and around the cervix. The batteries 16 are either embedded within the enlarged rim portion 12 or otherwise mounted thereon in a safe and secure non-obtrusive manner. Each battery 16 has one of its terminals electrically connected to the bus bar 17 and the remaining opposite terminal connected to the bus bar 18. In the FIG. 2 arrangement, the positive terminal of the battery 16 is connected to the bus bar 17 and the negative terminal of the battery is connected to the bus bar 18. Depending upon the current rating desired from the device, an additional number of electric cells such as 16 similarly can be embedded in other circular segments of the enlarged rim portion 12 and respectively interconnected with the bus bars 17 and 18 in the same manner as shown in FIG. 2.

As best shown in FIGS. 2, 3 and 3A, a plurality of spaced-apart, electrically conductive electrodes 19P and 19N are formed on the interior surfaces of the cervical cap 11 and preferably are fabricated from platinum wire, platinum alloys or platinum coated polymer material or other suitable biologically inert, electrically conductive material which is compatible with human and other animal tissue. The spacing between the electrodes preferably is of the order of one milli-inch (one mil) which also is their approximate width. The body of the cervical cap may be formed from a latex or other medical grade elastomer or similar material which is relatively flexible, electrically insulating and has a smooth outer surface. Similar to the bus bars 17 and 18, the spaced-apart electrically conductive electrodes 19P and 19N are formed on the surfaces of the cervical cap so as to be exposed to any cervical mucous fluid or male semen which might surround or seep into the interior of the cap.

The spaced-apart electrodes in the FIGS. 1-3 embodiment of the invention are shaped somewhat similar to the ribs of an umbrella and extend upwardly from respective ones of the circular bus bar terminal conductors 17 and 18, respectively to within the vicinity of the conductive plate members 14 and 15 surrounding the central opening 13 in the apex of the cap. Selected ones of the alternate electrodes 19P and 19N extend up to and contact a respective plate member 14 or 15. The electrodes labeled 19P all extend down and are integrally formed with or contact the circular bus bar conductor 17 which has a positive polarity potential supplied to it by a miniaturized cell 16 embedded in the enlarged rim portion 12 circumferentially surrounding the open mouth end of the cervical cap. The electrodes 19N on the other hand are insulatingly bridged over the upper circular bus bar member 17 and extend down to and contact the negative polarity circular bus bar conductor 18 as best shown in FIGS. 3 and 3A of the drawings.

As best seen in FIG. 2, those electrode members 19P which are circumferentially located on the same side of cervical cap 11 as the conductive plate member 15, extend all the way up to and engage plate member 15 so as to be electrically connected to it and supply it with positive polarity electric potential. In contrast, those negative polarity electrodes 19N which are on the same side of the periphery of cap 11 as the plate member 15, do not extend all the way to the plate member but terminate short of it so as maintain electrical isolation between the 19N electrodes and the 19P electrodes. In contrast, on the opposite side of the cap it is the 19N electrodes which extend up to, contact and are electrically connected to the electrically conducting plate member 14 so as to supply it with negative polarity energizing potential, and the positive polarity electrodes 19P stop short of the plate member 14.

The embodiment of the invention shown in FIGS. 1-3 can be semi-permanently implanted over the cervix either by the user or preferably by an experienced obstetrician or gynecologist and left there for prolonged periods of use. The presence of the central opening 13 at the apex of the cap permits body fluids discharged from the cervical canal to flow out through the opening thus allowing the extended usage period.

The presence of mid-cycle fluids in the cervical canal and at the mouth of the cervix, as explained in U.S. Pat. No. 4,616,640, or the presence of male semen, functions as an electrolyte in which electrostatic lines of force are established by the spaced-apart, oppositely charged electrode members 19P and 19N as well as the conductive bus bar members 17 and 18. As explained earlier, it is not now known what the exact phenomenon is that prevents sperm from penetrating through the electric field. Hypothetically, it is known that male sperm are electrically charged so that the presence of the strong electric field between the spaced-apart plate members 14 and 15, could cause the sperm to be attracted to one or the other of the plate members and are thereby prevented from travelling further up the cervical canal. Alternatively, it is conceivable that the presence of the strong electric field across the spaced-apart plate members induces ion current flow of the order of ten to twenty-five microamps (for example) or greater which adversely effects the sperm in such a manner as to prevent further movement of the sperm through the opening 13 and into the cervical canal opening. Similarly, electrical forces and ion current flow are induced between the electrode members 19P and 19N as well as the conductive bus bar members 17 and 18 which act in the same manner but will not be quite so intense as those concentrated across the spacedapart plate members 14 and 15 on opposite sides of the central opening 13.

FIG. 4 is a top plan view of a preferred embodiment of the invention. In FIG. 4 an electrical cervical cap 11, similar to the embodiment of FIGS. 1-3, also has an enlarged rim portion 12 circumventing its open mouth end and has a plurality of arcuately curved conductive electrodes 19P and 19N extending upwardly from the rim portion 12 in a manner similar to that described in FIGS. 1 and 2. However, in the FIG. 4 embodiment (as best seen in FIG. 4A), the alternate electrodes 19P and 19N preferably are fabricated from a conductive polymer and are integrally formed into the side walls of cervical cap 11 by a suitable injection molding process so that the conductive electrodes 19P and 19N extend through the thickness of the cap 11 and have both their exterior and interior surfaces exposed to human fluids in the vagina as well as to fluids in or about the cervical canal while the contraceptive devise is being worn. The upper ends of electrodes 19P and 19N terminate in a closed tip portion 21 located at the apex of the cervical cap 11 that is formed integrally from the same medical grade elastomer material from which the cervical cap 11 itself is fabricated. Thus, there is no opening in the apex of the electrical cervical cap of FIGS. 4 and 4A through which fluids can escape. Accordingly, the embodiment shown in FIG. 4 can be used only for short intervals of time. Since the tip portion 21 is of solid insulating material, the adjacent alternate polarity electrodes 19P nd 19N extend all the way up to and engage the side edges of the insulating tip portion 21 so as to emanate therefrom in the manner of the spokes of the hub of wheel. The outward ends of the electrodes 19P and 19N terminate in suitable circumferentially extending bus bar terminal conductors such as shown at 17 and 18 in FIG. 3. Terminal bus bar conductors 17 and 18 are appropriately interconnected with a suitable number of miniaturized electrical cells 16 embedded in an enlarged circular rim portion 12 similar to the arrangement shown in FIGS. 1-3 or to the arrangement shown in FIGS. 5 and 6 to be described hereafter.

In use, the embodiment of the invention shown in FIGS. 4 and 4A, the device may be inserted with a suitable insertion device by the user, and left in place for only relatively short intervals of time during the mid-cycle period while having intercourse. The electrical field created between the opposite polarity electrode members 19P and 19N as well as between the circumferential conductive bus bar members 17 and 18 provide a protective electric field force that in the presence of cervical mucous fluid of the female user or semen of a male serves as an electrolyte and results in establishing an electric force field and/or ion current flow which impedes and prevents any sperm and entrained bacteria or virus from passing between the interior surfaces of the cervical cap and the exterior of the cervix and into the cervical canal.

Figure 5:
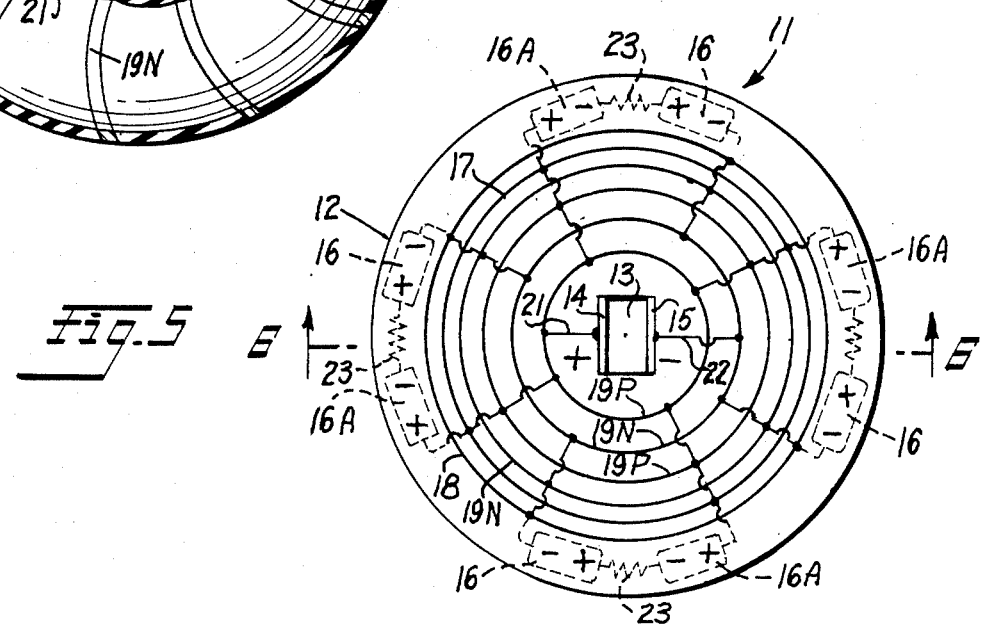
FIG. 5 is a diagrammatic top plan view of still another embodiment of an electric cervical cap contraceptive device according to the invention.

FIGS. 5 and 6 illustrate still another embodiment of the invention which is quite similar in many respects and physical structure to the embodiments of the invention shown in FIGS. 1-3 and 4 and 4A. FIG. 5 is a top plan view of an electrical cervical cap according to the invention which has only exterior mounted electric field producing electrodes 19P and 19N. FIGS. 5 and 6 differ from FIGS. 1-4A further in that the spaced-apart, oppositely poled electric field producing electrodes 19P and 19N are formed around the exterior circumference of the cervical cap 11 in the same manner as parallels of latitude which encircle the earth. A central opening 13 is formed in the apex of the cervical cap which is rectangular in nature and has spaced-apart electrically conductive plate members 14 and 15 disposed on opposite longer sides of the rectangular-shaped opening 13. Exterior jumper conductors shown at 21 and 22 interconnect the oppositely poled electrodes 19P and 19N with respective ones of the exteriorly formed circumferentially extending bus bar conductors 17 and 18 and the spaced-apart conductive plate members 14 and 15, respectively.

FIGS. 5 and 6 also illustrate how two or more electrical cells such as 16 and 16A can be electrically interconnected in series circuit relationship between the circumferential conductive bus bars 17 and 18 to provide a higher voltage excitation potential across the two bus bars 17 and 18 (and hence the electrodes 19P and 19N) which is in excess of the voltage provided by any of the individual cells 16. For example, in the embodiment of the invention shown in FIGS. 1 and 3, the cells 16 all are connected in parallel across the circumferential conductive bus bars 17 and 18 as described earlier. Assuming that each individual cell provides an open circuit output voltage of 2.8 volts, then that will be the voltage established between the conductive bus bars 17 and 18 as well as the excitation voltages across the respective sets of spaced-apart, opposite polarity electrode members 19P and 19N and plate members 14 and 15. The total number of cells connected in parallel in this manner will determine the value of the ion current that flows between the electrodes.

As shown in FIGS. 5 and 6, two of the individual 2.8 volt electric cells have been interconnected in series circuit relationship between the circumferential bus bar conductors 17 and 18 and thus the voltage between the bus bars 17 and 18 and electrodes 19P and 19N would have a nominal value of 2 times 2.8 or 5.6 volts. By thus interconnecting any desired number of the cells 16 (within physical limits) in series circuit relationship, any desired excitation potential can be developed between the respective bus bars 17 and 18 and their interconnected spaced-apart, oppositely-poled electrode members 19P and 19N and plate members 14 and 15.

In the event that an intermediate voltage is desired, such as for example 5 volts as opposed to the 5.6 volts, a small resistor fabricated in integrated circuit form, such as shown at 23, may be inserted in the interconnection between the two series connected electric cells 16 and 16A. By appropriately tailoring the resistance value of the integrated resistor 23, the 5 volt voltage can be obtained across the circumferentially extending bus bars 17 and 18 and hence electrode members 19P and 19N. To prevent generation of too much heat in any one spot in the enlarged circular rim portion 12 of the cervical cap, in place of finite resistors such as shown at 23, the interconnecting conductive paths between the cells 16 and 16A can be so fabricated using known printed conductor technology so that they themselves serve as the distributed resistance value required to obtain the desired output excitation voltage value. In a similar manner, using techniques known to those skilled in the art, the ion current flow developed with a parallel cell connected embodiment of the invention, such as shown in FIGS. 1-3, can be similarly tailored by varying the number of cells 16 and the resistance value of their interconnections to provide a desired ion current value for optimum results.

While the conductive electrode members 19P and 19N as well as the circumferential projecting bus bars 17 and 18 and the interconnecting jumper conductors such as 21 and 22 all have been described as printed circuit conductors, it should be understood that this term is used in a generic sense to cover the formation of such conductors by electro deposition or chemical deposition techniques as well as printing techniques with conductive inks or conductive paints, injecting molding of conductive polymers, molding of wires, or other known methods of fabricating conductive paths on background insulating material surfaces. Further, while the cervical cap 11 has been described as being fabricated from a latex-type material, it should be understood and this is true for all the embodiments, that any suitable medical grade elastomer such as a latex or silicon or other similar substance can be employed in fabricating the base cervical cap structure in a known manner.

FIG. 7 is a cross-sectional view of another embodiment of an electrical generally rounded, resilient canopy-like protective enclosure for the cervix that comprises a novel electrical diaphragm having a disc-shaped body member 111 integrally formed with a rim portion 12 from latex or other suitable medicalgrade elastomer or similar material. FIG. 8 of the drawings is a top plan view of the electrical diaphragm shown in FIG. 7. The electrical diaphragm of FIGS. 7 and 8 includes circumferentially formed, electrically conductive, terminal bus bar members 17 and 18 similar to those formed on the electrical cervical cap embodiments of the invention. The circumferential, terminal bus bar conductors 17 and 18 are electrically excited from a plurality of electrical cells 16 which are molded into the outer, enlarged rim portion 12 circumferentially surrounding the open-mouth end of the diaphragm. Spaced-apart electrically conducting electrodes of different polarity 19P and 19N extend respectively from either the positive polarity terminal bus bar 17 or the negative polarity terminal bus bar 18 upwardly and along the inside concave surface of the disclike body of the diaphragm 111 in a manner quite similar to the electrical cervical cap species shown in FIGS. 1 and 2. There is a substantial difference however in that there is no central opening 13 formed in the central apex portion of diaphragm 111.

When it is inserted and placed in operation, the electrical diaphragm 111 functions in the same manner as described above with respect to the electrical cervical cap. FIG. 12 illustrates the main difference between the two different types of electrical canopy-like protective enclosures. As shown in FIG. 12, the electrical cervical cap 11 is designed to embrace more closely the neck of the cervix 100 of the uterus 101 where the cervix projects into the vagina 102. Thus, the electrical cervical cap fits more closely over the opening 103 to the cervical canal in cervix 100 tnan does the electrical diaphragm 111 as shown schematically in FIG. 12 and more realistically in FIG. 11 of the drawings. It is also possible to design the electrical diaphragm so that it can be inserted further down in the vagina as shown at 111A in FIG. 12. While thus inserted, the electrical field forces developed by the electrical diaphragm 111A would be further away from the opening 103 to the cervical canal, but would be dispersed through more of the mucous fluid or semen contained within the vagina 102.

FIGS. 9 and 10 of the drawings illustrate a different species of the electrical diaphragmtype contraceptive device according to the invention wherein a central opening 13 is formed in the apex of the inwardly concave disc-type body member 111 that comprises the diaphragm. The electrical diaphragm of FIGS. 9 and 10 otherwise is similar in construction to the embodiment shown in FIGS. 7 and 8 except that certain of the internal electrode members 19P and 19N extend up to and electrically contact spaced-apart plate members 14 and 15 on opposite sides of the central opening 13. The spaced-apart opposite polarity potential plate members 14 and 15 on the outer convex surface of disc-like body member 111 are connected to respective sets of opposed concentric rings 19P and 19N as shown in FIG. 2, alternative ones of which are connected via a jumper conductor pathway 21 to the positive polarity plate member 15 and the remaining ones of which are connected via a jumper conductor pathway 22 to the negative polarity plate member 14. Thus, the embodiment of the invention shown in FIGS. 9 and 10 produce an electric field force both internally on the concave side of the diaphragm 111 and externally on the convex side which will have effect within the vagina generally. Here again, the species of the invention shown in FIGS. 9 and 10 can be mounted within the vagina either as shown at 111 in FIG. 12 or at 111A depending upon its particular design parameters and desired usage.

From the foregoing description, it will be appreciated that the invention provides a new and improved electrical canopy-like enclosure comprised by an electrical cervical cap or an electrical diaphragm contraceptive device for practicing a novel method of birth control which employs the introduction of an electrical force into and around the cervical canal of a female through the medium of either an electrical cervical cap or electrical diaphragm appropriately designed and arranged to develop an electrical field force in the vicinity of the cervix in and around the mouth of the opening to the cervical canal.

COMMERCIAL APPLICABILITY

The invention describes a new practical electrical cervical cap and electrical diaphragm contraceptive devices and birth control method for use by human females as well as the female of most quadrupeds and other mammals. The invention finds its greatest applicability within the family planning activities of the medical profession.

Having described several embodiments of new and improved electrical cervical cap and electrical diaphragm-type contraceptive devices and method for birth control in accordance with the invention, it is believed obvious that other modifications and variations of the invention will be suggested to those skilled in the art in the light of the above teachings. It is therefor to be understood that changes may be made in the particular embodiments of the invention described which are within the full intended scope of the invention as defined by the appended claims.

What is claimed is:

1. An electrical contraceptive device comprising an electrical generally rounded, resilient canopy-like protective enclosure for the cervix opening leading to the cervical canal and having a set of spaced-apart electrically conductive electrodes of biologically inert material compatible with human and other animal tissue formed thereon and means for supplying an electromotive force of known voltage and current rating across the set of electrodes from an independent source of electric potential.

2. An electrical contraceptive device according to claim 1 wherein the means for supplying an electromotive force of known voltage and current capacity is comprised by one or more miniaturized electrical cells secured within an enlarged rim portion formed around an open mouth end of the electrical canopy-like protective enclosure.

3. An electrical contraceptive device according to claim 1 wherein the spaced-apart electrically conductive electrodes are formed either on the exterior or interior surfaces of the electrical canopy-like protective enclosure or both and are exposed to human fluid on or about the cervix and the opening to the cervical canal which serves as an electrolyte for establishing and maintaining electromotive lines of force through the fluids.

4. An electrical contraceptive device according to claim 2 wherein the spaced-apart electrically conductive electrodes are formed either on the exterior or the interior surfaces of the electrical canopy-like protective enclosure or both and are exposed to human fluid on or about the cervix and the opening to the cervical canal which serves as an electrolyte for establishing and maintaining electromotive lines of force through the fluids.

5. An electrical contraceptive device according to claim 1 wherein the electrically conductive electrodes are comprised by two different sets of electrical conductors that are formed on the electrical canopy-like protective enclosure and that are spaced-apart from each other with the electrodes of one set being electrically insulated from the electrodes of the remaining set and each set of electrodes being supplied from circumferentially extending electrical bus bar terminal conductors formed in an enlarged rim surrounding an open mouth end of the electrical canopy-like protective enclosure which also supports miniaturized electrical cells having their respective opposite polarity terminals connected to one or the other of the circular bus bar terminal conductors supplying the respective sets of electrically conductive electrodes.

6. An electrical contraceptive device according to claim 4 wherein the electrically conductive electrodes are comprised by two different sets of electrical conductors formed on tne surface of the electrical canopy-like protective enclosure and that are spaced-apart from each other with the electrodes of one set being electrically insulated from the electrodes of the remaining set and each set of electrodes being supplied from a respective circumferentially extending electrical bus bar terminal conductor formed in an enlarged rim surrounding the open mouth end of the electrical canopy-like protective enclosure which also supports miniaturized electrical cells having their respective opposite polarity terminals connected to one or the other of the circular bus bar terminal conductors supplying a respective set of electrically conductive electrodes, and wherein the sets of spaced-apart electrically conductive electrodes extend upwardly from the respective circular electrical bus bar conductors in the manner of the ribs of an umbrella.

7. An electrical contraceptive device according to claim 5 wherein the electrically conductive electrodes encircle the electrical canopy-like protective enclosure at different distances measured along its center axis similar to the manner in which parallels of latitude encircle the earth and wherein jumper conductors are provided to connect respective spaced-apart ones of the electrically conductive electrodes to opposite terminals of at least one miniaturized electric cell mounted in the enlarged rim formed around an open mouth end of the electrical canopy-like protective enclosure.

8. An electrical contraceptive device according to claim 4 wherein the electrically conductive electrodes encircle the electrical canopy-like protective enclosure at different distances measured along its center axis similar to the manner in which parallels of latitude encircle the earth and wherein jumper conductors are provided to connect respective spaced-apart ones of the electrically conductive electrodes to opposite polarity terminals of at least one miniaturized electric cell mounted in the enlarged rim formed around an open mouth end of the electrical canopylike protective enclosure.

9. An electrical contraceptive device according to claim 1 wherein there is a central opening in the apex of the electrical canopy-like protective enclosure through which fluids may pass and wherein a set of spaced-apart electrically conductive plate members are formed on the sides of the opening in opposed confronting relationship which are electrically isolated one from the other and wherein alternate ones of the set of spacedapart electrically conductive electrodes are connected to one of the spaced-apart plate members formed on one side of the opening and the remaining alternate ones of the set of spaced-apart electrically conductive electrodes are electrically connected to the remaining conductive plate member on the opposite side of the opening.

10. An electrical contraceptive device according to claim 5 wherein there is a central opening in the apex of the electrical canopy-like protective enclosure through which fluids may pass and wherein a set of spaced-apart electrically conductive plate members are formed on the sides of the opening in opposed confronting relationship which are electrically isolated one from the other and wherein alternate ones of the set of spacedapart electrically conductive electrodes are connected to one of the spaced-apart plate members formed on one side of the opening and the remaining alternate ones of the set of spaced-apart electrically conductive electrodes are electrically connected to the remaining conductive plate member on the opposite side of the opening.

11. An electrical contraceptive device according to claim 6 wherein there is a central opening in the apex of the electrical canopy-like protective enclosure through which fluids may pass and wherein a set of spaced-apart electrically conductive plate members are formed on the sides of the opening in opposed confronting relationship which are electrically isolated one from the other and wherein alternate ones of the set of spacedapart electrically conductive electrodes are connected to one of the spaced-apart plate members formed on one side of the opening and the remaining alternate ones of the set of spaced-apart electrically conductive electrodes are electrically connected to the remaining conductive plate member on the opposite side of the opening.

12. An electrical contraceptive device according to claim 1 wherein the electrical canopy-like protective enclosure is an electrical cervical cap.

13. An electrical contraceptive device according to claim 5 wherein the electrical canopy-like protective enclosure is an electrical cervical cap.

14. An electrical contraceptive device according to claim 10 wherein the electrical canopy-like protective enclosure is an electrical cervical cap.

15. An electrical contraceptive device according to claim 1 wherein the electrical canopy-like protective enclosure is an electrical diaphragm.

16. An electrical contraceptive device according to claim 5 wherein the electrical canopy-like protective enclosure is an electrical diaphragm.

17. An electrical contraceptive device according to claim 10 wherein the electrical canopy-like protective enclosure is an electrical diaphragm.

18. The method of birth control which comprises providing an electrical force within the vagina on or about the cervical canal of a female human or other mammal by means of an electrical generally rounded, resilient canopy-like protective enclosure fitted in the vagina and covering the opening in the cervix to the cervical canal of a female human being or other female mammal, said electrical generally rounded, resilient canopy-like protective enclosure having formed thereon a set of spaced-apart electrically conductive electrodes of biologically inert conductive material compatible with human and other animal tissue, and providing an electromotive force of known voltage and current rating across the set of conductive electrodes from an independent source of electric potential.

19. The method of birth control according to claim 18 wherein the means for supplying an electromotive force of known voltage and current rating is comprised by one or more miniaturized electrical cells secured within an enlarged rim portion formed around an open mouth end of the electrical canopy-like protective enclosure.

20. The method of birth control according to claim 18 wherein the spaced-apart electrically conductive electrodes are formed either on the exterior or the interior surfaces of the electrical canopy-like protective enclosure or both and are exposed to human fluids in the vigina on or about the cervix and cervical canal which serve as an electrolyte for establishing and maintaining electromotive lines of force through the fluids.

21. The method of birth control according to claim 18 wherein the means for supplying an electromotive force of known voltage and current rating is comprised by one or more miniaturized electrical cells secured within an enlarged rim portion formed around an open mouth end of the electrical canopy-like protective enclosure, and wherein the spaced-apart electrically conductive electrodes are formed either on the exterior or the interior surfaces of the electrical canopy-like protective enclosure and are exposed to human fluids in the vigina on or about the cervix and cervical canal which serve as an electrolyte for establishing and maintaining electromotive lines of force through the fluids.

22. A method of birth control according to claim 18 wherein the electrically conductive electrodes are comprised by two different sets of electrical conductors that are formed either on the exterior or the interior surfaces of the electrical canopy-like protective enclosure or both and that are spaced-apart from each other with the electrodes of one set being electrically insulated from the electrodes of the remaining set and each set of electrodes being supplied from electrical bus bar terminal conductors formed in an enlarged rim surrounding an open mouth end of the electrical canopy-like protective enclosure which also supports miniaturized electrical cells having their respective opposite polarity terminals connected to one or the other of the bus bar terminal conductors supplying the respective sets of electrically conductive electrodes.

23. A method of birth control according to claim 21 wherein the electrically conductive electrodes are comprised by two different sets of electrical conductors that are formed either on the exterior or the interior surface of the electrical canopy-like protective enclosure or both and that are spaced-apart from each other with the electrodes of one set being electrically insulated from the electrodes of the remaining set and each set of electrodes being supplied from electrical bus bar terminal conductors formed in an enlarged rim surrounding an open mouth end of the electrical canopy-like protective enclosure which also supports miniaturized electrical cells having their respective opposite polarity terminals connected to one or the other of the bus bar terminal conductors supplying the respective sets of electrically conductive electrodes, and wherein the sets of spaced-apart electrically conductive electrodes extend upwardly from the respective electrical bus bar conductors in the manner of the ribs of an umbrella.

24. The method of birth control according to claim 22 wherein the electrically conductive electrodes encircle the electrical canopy-like protective enclosure at different distances measured along its center axis similar to the manner in which parallels of latitude encircle the earth and wherein jumper conductors are provided to connect respective spaced-apart ones of the electrically conductive electrodes to opposite terminals of at least one miniaturized electric cell mounted in the enlarged rim formed around an open mouth end of the electrical canopy-like protective enclosure.

25. The method of birth control according to claim 18 wherein the means for supplying an electromotive force of known voltage and current capacity is comprised by one or more miniaturized electrical cells secured within an enlarged rim portion formed around an open mouth end of the electrical canopy-like protective enclosure, the spaced-apart electrically conductive electrodes are formed either on the exterior or the interior surfaces of the electrical canopy-like protective enclosure or both and are exposed to human fluids within the vagina on or about the cervix and the opening to the cervical canal which serve as an electrolyte for establishing and maintaining electromotive lines of force through the fluids, and wherein the electrically conductive electrodes encircle the electrical canopy-like protective enclosure at different distances measured along its center axis similar to the manner in which parallels of latitude encircle the earth and wherein jumper conductors are provided to connect respective spaced-apart ones of the electrically conductive electrodes to opposite terminals of at least one miniaturized electric cell mounted in an enlarged rim formed around an open mouth end of the electrical canopy-like protective enclosure.

26. The method of birth control according to claim 18 wherein there is a central opening in the apex of the electrical canopy-like protective enclosure through which fluids may pass and wherein a set of spaced-apart electrically conductive plate members are formed on the sides of the opening in opposed confronting relationship which are electrically isolated one from the other and wherein alternate ones of the set of spaced-apart electrically conductive electrodes are connected to one of the spaced-apart plate members formed on one side of the opening and the remaining alternate ones of the set of spaced-apart electrically conductive electrodes are electrically connected to the remaining conductive plate member formed on the opposite side of the central opening in the apex of the electrical canopy-like protective enclosure.

27. The method of birth control according to claim 26 wherein the electrically conductive electrodes are comprised by two different sets of electrical conductors formed around the surface of the electrical canopy-like protective enclosure and that are spaced-apart from each other with the electrodes of one set being electrically insulated from the electrodes of the remaining set and each set of electrodes being supplied from a respective circumferentially extending electrical bus bar terminal conductor formed in an enlarged rim surrounding an open mouth end of the electrical canopy-like protective enclosure which also supports miniaturized electrical cells having their respective opposite polarity terminals connected to one or the other of the circular bus bar terminal conductors supplying a respective set of electrically conductive electrodes, and wherein the sets of spaced-apart electrically conductive electrodes extend upwardly from the respective circular electrical bus bar conductors in the manner of the ribs of an umbrella.

28. The method of birth control according to claim 26 wherein the electrically conductive electrodes encircle the electrical canopy-like protective enclosure at different distances measured along its center axis similar to the manner in which parallels of latitude encircle the earth and wherein jumper conductors are provided to connect respective spaced-apart ones of the electrically conductive electrodes to opposite polarity terminals of at least one miniaturized electric cell mounted in an enlarged rim formed around an open mouth end of the electrical canopy-like protective enclosure.

29. The method of birth control according to claim 18 wherein the electrical canopy-like protective enclosure comprises an electrical cervical cap.

30. The method of birth control according to claim 22 wherein the electrical canopy-like protective enclosure comprises an electrical cervical cap.

31. The method of birth control according to claim 25 wherein the electrical canopy-like protective enclosure comprises an electrical cervical cap.

32. The method of birth control according to claim 26 wherein the electrical canopy-like protective enclosure comprises an electrical cervical cap.

33. The method of birth control according to claim 18 wherein the electrical canopy-like protective enclosure comprises an electrical diaphragm.

34. The method of birth control according to claim 22 wherein the electrical canopy-like protective enclosure comprises an electrical diaphragm.

35. The method of birth control according to claim 25 wherein the electrical canopy-like protective enclosure comprises an electrical diaphragm.

36. The method of birth control according to claim 26 wherein the electrical canopy-like protective enclosure comprises an electrical diaphragm.

* * * * *